(12) United States Patent
Ohkubo

(10) Patent No.: US 11,174,204 B2
(45) Date of Patent: Nov. 16, 2021

(54) LACTIC ACID BACTERIA, AND FEED, FERTILIZER, AND VIABLE BACTERIAL PREPARATION CONTAINING SAID LACTIC ACID BACTERIA

(71) Applicant: Takashi Ohkubo, Saga (JP)

(72) Inventor: Takashi Ohkubo, Saga (JP)

( * ) Notice: Subject to any disclaimer, the term of this patent is extended or adjusted under 35 U.S.C. 154(b) by 258 days.

(21) Appl. No.: 16/332,977

(22) PCT Filed: Sep. 12, 2017

(86) PCT No.: PCT/JP2017/032818
§ 371 (c)(1),
(2) Date: Mar. 13, 2019

(87) PCT Pub. No.: WO2018/051967
PCT Pub. Date: Mar. 22, 2018

(65) Prior Publication Data
US 2019/0270681 A1 Sep. 5, 2019

(30) Foreign Application Priority Data

Sep. 13, 2016 (JP) .............................. JP2016-178146
Jun. 30, 2017 (JP) .............................. JP2017-128717

(51) Int. Cl.
| | | |
|---|---|---|
| *A23K 10/18* | (2016.01) | |
| *A61K 35/741* | (2015.01) | |
| *C05F 11/08* | (2006.01) | |
| *C12N 1/20* | (2006.01) | |
| *A01G 7/06* | (2006.01) | |
| *A23L 33/135* | (2016.01) | |

(52) U.S. Cl.
CPC .............. *C05F 11/08* (2013.01); *A01G 7/06* (2013.01); *A23K 10/18* (2016.05); *A61K 35/741* (2013.01); *C12N 1/20* (2013.01); *A23L 33/135* (2016.08)

(58) Field of Classification Search
None
See application file for complete search history.

(56) References Cited

FOREIGN PATENT DOCUMENTS

| JP | 2009-100677 A | 5/2009 |
|---|---|---|
| JP | 2009-225792 A | 10/2009 |
| JP | 5597237 B2 | 10/2014 |
| JP | 2016-123382 A | 7/2016 |
| JP | 5958985 B1 | 8/2016 |
| JP | 6045743 B1 | 12/2016 |

OTHER PUBLICATIONS

International Search Report for PCT/JP2017/032818 issued by ISA/JP dated Oct. 10, 2017.

*Primary Examiner* — Padmavathi Baskar
(74) *Attorney, Agent, or Firm* — Kubotera & Associates, LLC

(57) ABSTRACT

An object is to provide lactic acid bacteria that can be applicable to feed, fertilizers, live bacterial preparations, probiotics, etc. The lactic acid bacteria are identified and deposited under the accession numbers of NITE (National Institute of Technology and Evaluation) P-02313, NITE P-02314, NITE P-02490, NITE P-02491, and NITE P-02492. In addition, another object is to provide feed, fertilizers and live bacterial preparations containing the lactic acid bacterium/bacteria of the invention. According to studies, it is confirmed that the lactic acid bacteria are proliferated in animals including human, plants, etc. without being destroyed. According to studies, it is also confirmed that the lactic acid bacteria are proliferated in water, soil, etc. without being destroyed. Therefore, the lactic acid bacteria can be widely applicable in feed, fertilizers, live bacterial preparations, etc.

4 Claims, No Drawings

LACTIC ACID BACTERIA, AND FEED, FERTILIZER, AND VIABLE BACTERIAL PREPARATION CONTAINING SAID LACTIC ACID BACTERIA

BACKGROUND OF THE INVENTION AND RELATED ART STATEMENT

The present invention relates to lactic acid bacteria. The present invention also relates to feed, fertilizers and live bacterial preparations (or probiotics) containing the lactic acid bacterium.

Lactic acid bacteria are generally referred to bacteria that produce lactic acid through metabolic activities thereof. It has been known that each of lactic acid bacteria tends to exhibit a different characteristic.

Conventionally, bacteria with specific characteristics such as lactic acid bacteria have been extracted so that their characteristics have been studied to develop products including drugs, food and drink, etc. taking advantage of such characteristics. (see Patent Reference for example).

Patent Reference: Japanese Patent Publication No. 5,597,237

Generally speaking, conventionally known lactic acid bacteria are restricted from proliferation by an environmental condition. Therefore, in many cases, lactic acid bacteria are found to be not suitable and difficult for making feed, fertilizers, live bacterial preparations, etc.

In view of the problem described above, an object of the present invention is to provide lactic acid bacteria through diligently engaged researches and studies in extractions of lactic acid bacteria.

SUMMARY OF THE PRESENT INVENTION

According to a first aspect of the present invention, a lactic acid bacterium is identified and deposited under the accession number of NITE (National Institute of Technology and Evaluation) P-02313.

According to a second aspect of the present invention, a lactic acid bacterium is identified and deposited under the accession number of NITE P-02314.

According to a third aspect of the present invention, a lactic acid bacterium is identified and deposited under the accession number of NITE P-02490.

According to a fourth aspect of the present invention, a lactic acid bacterium is identified and deposited under the accession number of NITE P-02491.

According to a fifth aspect of the present invention, a lactic acid bacterium is identified and deposited under the accession number of NITE P-02492.

According to a sixth aspect of the present invention, feed contains the lactic acid bacterium/bacteria according to any one of the first to fifth aspect of the present invention.

According to a seventh aspect of the present invention, a fertilizer contains the lactic acid bacterium/bacteria according to any one of the first to fifth aspect of the present invention.

According to an eighth aspect of the present invention, a live bacterial preparation (or probiotics) contains the lactic acid bacterium/bacteria according to according to any one of the first to fifth aspect of the present invention.

The lactic acid bacteria of the present invention are effectively applicable for feed, fertilizers, and live bacterial preparations.

DETAILED DECSRIPTION OF THE PREFERRED EMBODIMENTS

Isolation Example 1

After processing a fish with a special method for fermentation, the presence of a variety of bacteria was detected in the fish meat, etc. Among the bacteria thus detected, the presence of lactic acid bacteria was detected.

Afterward, it was decided to isolate only the lactic acid bacteria and conduct the isolation at Techno Suruga Laboratory Co., Ltd. (330 Nagasaki, Shimizu-ku, Shizuoka-shi, Shizuoka, Japan).

To isolate the bacteria, isolation and culturing were conducted under the following conditions. Thereafter, observation of the colonies was performed, and gram staining and catalase test were performed.

Culturing Conditions
  Culturing medium: MRS agar (Oxoid, Hampshire, UK)+3% NaCl
  Culturing temperature: 30° C.
  Culturing period: 3 days
  Diluent: Saline solution
  Dilution factor: Undiluted to $10^4$
  Isolation method: Dilution plate method
  Other conditions Anaerobic
Colony Observation
  Observed the resultant colonies using a stereo microscope SZG10 (Olympus, Tokyo, Japan).
Gram Staining
  Fiber G "Nissui" (Nissui Pharmaceutical Co., Ltd., Tokyo, Japan) was used in the gram staining and an optical microscope BX51 (Olympus, Tokyo, Japan) was used as a microscope.
Catalase Test
  Using 3% hydrogen peroxide solution, the test was conducted and it was determined that the result was positive if air bubbles were produced.

By the isolation and culturing, growth of a plurality of colonies having different characteristics was observed. For the isolated strains, gram staining and the catalase test were conducted. The bacteria that were gram positive and catalase negative were determined as lactic acid bacteria. As a result, colonies of two types of bacteria that were possibly lactic acid bacteria were isolated. Hereinafter, those bacteria are referred to as SIID17126-L1 and SIID17126-L2, respectively.

Next, an identification test was conducted for the respective bacteria (SIID17126-L1 and SIID17126-L2). The identification test was conducted by Techno Suruga Laboratory Co., Ltd. conducted based on our request for their Bacterial Premium Test.

In the identification test, the bacteria were cultured under the following conditions and 16S rDNA sequence analysis, morphological observation and physiological/biochemical tests (bacterial first-stage test and bacterial second-stage test) were conducted to estimate the group that the bacteria belong to.

Culturing Conditions
  Culturing medium: MRS agar (Oxoid, Hampshire, UK)
  Culturing temperature: 30° C.
  Culturing period: 48 hours
  Diluent: Saline solution
  Other conditions Anaerobic
16S rDNA (16S rRNA Gene) Sequence Analysis
  The procedures from PCR amplification to cycle sequencing were performed based on the respective protocols.

DNA extraction:
Achromopeptidase (Wako Pure Chemical Industries, Ltd., Osaka, Japan)
PCR amplification:
PrimeSTAR HS DNA Polymerase (Takara Bio Inc., Shiga, Japan)
Cycle sequencing:
BigDye Terminator v3.1 Cycle Sequencing Kit (Applied Biosystems, California, U.S.A)
Primer used this time:
PCR amplification: 9F, 1510R
Sequencing: 9F, 785F, 802R, 1510R Sequencer:
ABI PRISM 3130xl Genetic Analyzer System (Applied Biosystems, California, U.S.A)
Sequencing software:
ChromasPro 1.7 (Technelysium Pty Ltd., Tewantin, AUS)
BLAST homology search and simplified molecular phylogenetics:
DNA database for microbial identification D BOBA10.0 (Techno Suruga Laboratory Co., Ltd., Shizuoka, Japan)
International Nucleotide Sequence Database Collaboration (GenBank/DDBJ/EMBL)

Bacterial First-Stage Test

Based on the morphological observation using an optical microscope BX50F4 (Olympus, Tokyo, Japan) and the method by Barrow et al. (BARROW, (G.I.) and FELTHAM, (R.K.A.): Cowan and Steel's Manual for the Identification of Medical Bacteria. 3rd Ed. 1993, Cambridge University Press), catalase reaction, oxidase reaction, acid/gas production from glucose, and oxidation/fermentation of glucose were tested.

Bacterial Second-Stage Test

For this test, an API 20 Strep kit (bioMérieux, Lyon, France) was used. Additional experiments were also conducted, according to technical cooperation matters with NCIMB Ltd. (United Kingdom, http://www.ncimb.co.uk/) and related references regarding classification and identification.

The result of the 16S rDNA sequence analysis suggested that SIID17126-L1 may belong to *Enterococcus*, more specifically *E. devriesei, E. pseudoavium*, or *E. viikkiensis*.

In addition, according to the result of the bacterial first-stage test, SIID17126-L1 had properties that were consistent with those of *Enterococcus*. According to the result of the bacterial second-stage test, SIID17126-L1 was recognized to have different properties from those of *E. pseudo avium*, but have properties that were consistent with those of *E. devriesei* or those of *E. viikkiensis*.

Based on the above results, it was estimated that SIID17126-L1 belongs to *Enterococcus viikkiensis* or *Enterococcus devriesei*.

In addition, the results of the sequencing analysis of 16SrDNA suggested that SIID17126-L2 may belong to *L. latis*, possibly belonging to *Lactococcus*, more specifically *L. lactis* subsp. *lactis*.

In addition, according to the results of the bacterial first-stage test, SIID17126-L1 had properties that were consistent with those of *Lactococcus*. According to the results of the bacterial second-stage test, SIID17126-L1 had properties that were consistent with those of *Lactococcus lactis* subsp. *lactis*.

Based on the above results, it is determined that SIID17126-L2 belongs to *Enterococcus lactis* subsp. *lactis*.

Those lactic acid bacteria (SIID17126-L1 and SIID17126-L2) have been deposited as follows:

Depository Institution: NITE (National Institute of Technology and Evaluation) Patent Microorganisms Depository (NPMD) (2-5-8 Kazusa Kamatari, Kisaradu-shi, Chiba, Japan 292-0818)
Accession Date: Aug. 2, 2016
Accession Numbers: NITE P-02313 for SIID 17126-L1
NITE P-02314 for SIID 17126-L2
Here, those lactic acid bacteria have been transferred to international depository as follows:
Accession Numbers: NITE BP-02313 for SIID 17126-L1
NITE BP-02314 for SIID 17126-L2

The above-described lactic acid bacteria (SIID17126-L1 and SIID17126-L2) were confirmed to have the following properties. Here, detections of the lactic acid bacteria described below were performed at Japan Food Research Laboratories (52-1 Motoyoyogi-cho, Shibuya-ku, Tokyo) or at Saga Environmental Science Inspection Association (1-4-2 Hikari, Saga-shi, Saga).

Isolation Example 2

Processing fish by a special method for fermentation, the presence of variety of bacteria was detected in the fish meat, etc. In the bacteria, the presence of lactic acid bacteria was detected.

Accordingly, it was decided to isolate only the lactic acid bacteria. The isolation of the lactic acid bacteria was performed by Techno Suruga Laboratory Co., Ltd. (330 Nagasaki, Shimizu-ku, Shizuoka-shi, Shizuoka, Japan) based on our request.

In the isolation of the bacteria, isolation and culturing of the bacteria were conducted under the similar conditions to those in the above-described Isolation Example 1. Thereafter, observation of the resultant colonies was performed, and gram staining and catalase test were conducted.

By the isolation and the culturing, growth of a plurality of colonies having different properties was observed. For the isolated strains, gram staining and the catalase test were conducted. The bacteria that were gram positive and catalase negative were determined as lactic acid bacteria. As a result, colonies of three types of bacteria that were possibly lactic acid bacteria were isolated. Hereinafter, those bacteria are referred to as SIID21336-L1, SIID21336-L2 and SIID21336-L3, respectively.

Next, an identification test was conducted for the respective bacteria (IID21336-L1, SIID21336-L2 and SIID21336-L3). The identification test was conducted by Techno Suruga Laboratory Co., Ltd. based on our request for their Bacterial Premium Test.

In the identification test, the bacteria were cultured under the similar conditions to those of the above-described Isolation Example 1. Then, 16S rDNA sequence analysis, morphological observation and physiological/biochemical tests (bacterial first-stage test and bacterial second-stage test) were conducted to estimate the genus and species that the bacteria belong to from the results.

A result of the 16S rDNA sequence analysis suggested that SIID21336-L1 may belong to *Lactobacillus*, more specifically *L. brevis*.

In addition, according to the results of the bacterial first-stage test, SIID21336-L1 had properties that were consistent with those of *Lactobacillus*. According to the results of the bacterial second-stage test, SIID21336-L1 had consistent properties to those of *L. brevis*.

Based on the above results, it is determined that SIID21336-L2 belongs to *Lactobacillus brevis*.

A result of the 16S rDNA sequence analysis suggested that SIID21336-L2 may possibly belong to *Lactobacillus*, more specifically *Lactobacillus* sp. that was closely related to *L. plantarum*.

In addition, according to the results of the bacterial first-stage test, SIID17126-L1 had properties that were consistent with those of *Lactococcus*. According to the results of the bacterial second-stage test, SIID17126-L1 had properties that were consistent with those of *Lactococcus lactis* subsp. *lactis*.

Based on the above results, it is determined that SIID21336-L2 belongs to *Lactobacillus* sp. that is closely related to *L. plantarum*.

A result of the 16S rDNA sequence analysis suggested that SIID21336-L3 may belong to *Enterococcus*, more specifically *E. casseliflavus*.

In addition, according to the results of the bacterial first-stage test, SIID21336-L3 had properties that were consistent with those of *Enterococcus*. According to the results of the bacterial second-stage test, SIID21336-L3 had properties that were consistent with those of *E. casseliflavus*.

Based on the above results, it is determined that SIID21336-L3 belongs to *Enterococcus casseliflavus*.

Those lactic acid bacteria (SIID21336-L1, SIID21336-L2 and SIID21336-L3) have been deposited as follows:
  Depository Institution:
  NITE (National Institute of Technology and Evaluation) Patent Microorganisms Depositary (NPMD) (2-5-8 Kazusa Kamatari, Kisaradu-shi, Chiba, Japan 292-0818)
  Accession Date: Jun. 12, 2017
  Accession Numbers:
  NITE P-02490 for SIID 21336-L1
  NITE P-02491 for SIID 21336-L2
  NITE P-02492 for SIID 21336 L2 21336-L3

[Properties]

The above-described lactic acid bacteria (SIID17126-L1, SIID17126-L2, SIID21336-L1, SIID21336-L2 and SIID21336-L3) were confirmed to have the following properties.

Here, detections of the lactic acid bacteria described below were performed at Japan Food Research Laboratories (52-1 Motoyoyogi-cho, Shibuya-ku, Tokyo) or at Saga Environmental Science Inspection Association (1-4-2 Hikari, Saga-shi, Saga).

(1) Feed

Giving feed not containing lactic acid bacteria to chickens, and their eggs were tested. As a result, the lactic acid bacteria were not detected from the eggs (yolks and egg whites).

In addition, adding representative commercially-available lactic acid bacteria (yogurt) to the above-described feed that did not contain the lactic acid bacteria, the feed was given to chickens and their eggs were tested. As a result, the lactic acid bacteria were not detected from the eggs (yolks and egg whites).

Furthermore, adding the lactic acid bacteria of the invention (SIID17126-L1, SIID17126-L2, SIID21336-L1, SIID21336-L2 or SIID21336-L3 alone or a mixture of at least two types of them) to the feed that did not contain lactic acid bacteria, the feed was given to chicken and their eggs were tested. As a result, the lactic acid bacterium/bacteria were detected from the eggs (yolks and egg whites).

From those results, it was found that the lactic acid bacteria of the invention (IID17126-L1, SIID17126-L2, SIID21336-L1, SIID21336-L2 and SIID21336-L3) can proliferate in mother chickens without being digested or destroyed if added in their bodies, and can be included in their yolks and egg whites of their eggs.

As described above, when the above-described lactic acid bacteria (SIID17126-L1, SIID17126-L2, SIID21336-L1, SIID21336-L2 and/or SIID21336-L3) are contained in feed, the bacteria can proliferate in animal bodies such as livestock and can be administered to the animals through eating the feed. In addition, even their baby birds or eggs, to which the feed was not directly given, can contain the lactic acid bacteria.

Accordingly, it can be understood that the feed may be applicable as a method of producing eggs containing lactic acid bacteria.

(2) Fertilizer(s)

Feeding fertilizer not containing the lactic acid bacteria to tomato seedlings, the resultant ripened tomatoes were tested. The tomatoes did not contain the lactic acid bacteria.

However, when the above-described lactic acid bacteria (SIID17126-L1, SIID17126-L2, SIID21336-L1, SIID21336-L2 or SIID21336-L3 alone or a mixture of at least two types of them) were added to the fertilizer that did not contain lactic acid bacteria and was fed as a fertilizer to tomato seedlings, the lactic acid bacteria were detected from the resultant ripened tomatoes.

Moreover, it was also confirmed that the tomatoes ripe satisfactorily faster than those seedlings, to which the fertilizer that did not contain the lactic acid bacteria was fed.

Accordingly, when the above-described lactic acid bacteria (SIID17126-L1, SIID17126-L2, SIID21336-L1, SIID21336-L2 and/or SIID21336-L3) are contained in a fertilizer, the lactic acid bacteria can proliferate inside the plants such as vegetables and can be administered to the grown plants through the fertilizer. In addition, the lactic acid bacteria can be also contained in even their resultant fruits.

Accordingly, it can be understood that the fertilizer may be also applicable as a method of producing vegetables containing lactic acid bacteria.

(3) Live Bacterial Preparation(s) or Probiotics

When the content of lactic acid bacterium was determined in seawater, river water (fresh water), brackish water (mixture of seawater and river water), light petroleum-added seawater and marine soil, lactic acid bacteria were not detected from any of them.

To the seawater, river water, brackish water, light petroleum-added seawater. marine soil, representative commercially-available lactic acid bacteria (yogurt) was added and left to stand. As a result, it was confirmed that the added lactic acid bacteria were destroyed.

However, when the above-described lactic acid bacteria (SIID17126-L1, SIID17126-L2, SIID21336-L1, SIID21336-L2 or SIID21336-L3 alone or a mixture of at least two types of them) were added to the seawater, river water, brackish water, light petroleum-added seawater and marine soil that did not contain lactic acid bacteria and left to stand, it was confirmed that the lactic acid bacteria added therein were not destroyed and proliferated.

Furthermore, the above-described lactic acid bacteria (SIID17126-L1, SIID17126-L2, SIID21336-L1, SIID21336-L2 or SIID21336-L3 alone or a mixture of at least two types of them) were added to live seaweed that was farm-raised in the seawater. As a result, the lactic acid bacteria were detected from the seaweed.

In addition, as also confirmed in the fertilizer of (2) above, the lactic acid bacteria were not destroyed even in the soil, to which the above-described lactic acid bacteria (SIID17126-L1, SIID17126-L2, SIID21336-L1, SIID21336-L2 or SIID21336-L3 alone or a mixture of at least two types of them) were added.

Therefore, it can be understood that the above-described lactic acid bacteria (SIID17126-L1, SIID17126-L2, SIID21336-L1, SIID21336-L2 or SIID21336-L3 alone or a mixture of at least two types of them) can be administered with water, soil or the like. In addition, the lactic acid bacteria (SIID17126-L1, SIID17126-L2, SIID21336-L1, SIID21336-L2 or SIID21336-L3 alone or a mixture of at least two types of them) can be used as a live bacterial preparation that can be administered as one of environmental measures to protect/maintain/restore/create biotope for human to ecologically live with plants, animals, organisms, etc.

(4) Food and/or Drink the above-described lactic acid bacteria (SIID17126-L1, SIID17126-L2, SIID21336-L1, SIID21336-L2 or SIID21336-L3 alone or a mixture of at least two types of them) was added to gastric acid and left it to stand. As a result, it was confirmed that the added lactic acid bacteria were not destroyed and remained live.

Therefore, it can be understood that the above-described lactic acid bacteria (SIID17126-L1, SIID17126-L2, SIID21336-L1, SIID21336-L2 or SIID21336-L3 alone or a mixture of at least two types of them) may be added to food and/or drink. In addition, the above-described lactic acid bacteria (SIID17126-L1, SIID17126-L2, SIID21336-L1, SIID21336-L2 or SIID21336-L3 alone or a mixture of at least two types of them) can be similarly added to medicines, dietary supplements, etc.

(5) Other Conditions

The above-described lactic acid bacteria (SIID17126-L1, SIID17126-L2, SIID21336-L1, SIID21336-L2 or SIID21336-L3 alone or a mixture of at least two types of them) may be applicable to a method of producing fish products such as sashimi (thin slices of fresh raw fish to eat as is) containing the lactic acid bacteria by extracting them from fish. In addition, it is also achievable to detoxify puffer toxin and it can be further applicable to a method of processing fish containing unsaturated fatty acid(s), nitrogen, phosphorus and/or potassium.

Furthermore, it can be also used in live bacterial preparations, fertilizers, feed, food, etc. as lactic acid bacteria containing five elements contained in fish (calcium, magnesium, nitrogen, phosphorus and potassium) and trace elements (iron, chlorine, manganese, zinc, copper, boron, molybdenum, and nickel).

What is claimed is:

1. A lactic acid bacterium deposited under an accession number of (National Institute of Technology and Evaluation) NITE P-02492,
   wherein said lactic acid bacterium is cultured with MRS agar at 30° C. and isolated with a dilution plate method.
2. Feed containing the lactic acid bacterium according to claim 1.
3. A fertilizer containing the lactic acid bacterium according to claim 1.
4. A live bacterial preparation or probiotic containing the lactic acid bacterium according to claim 1.

* * * * *